United States Patent [19]

Giannetti

[11] Patent Number: 4,947,838

[45] Date of Patent: Aug. 14, 1990

[54] SHELL-LIKE ORTHOPEDIC BRACE

[76] Inventor: Donato Giannetti, Via Virgilio Melandri, 184/E, Roma, Italy, 00155

[21] Appl. No.: 315,805

[22] Filed: Feb. 27, 1989

[51] Int. Cl.$^5$ ............................................. A61F 5/00
[52] U.S. Cl. ................................. 128/80 R; 128/89 R
[58] Field of Search .................... 128/80 C, 88, 80 F, 128/80 H, 80 R, 89 R, 90, 91

[56] References Cited

U.S. PATENT DOCUMENTS

| | | | |
|---|---|---|---|
| 2,501,903 | 3/1950 | Huggins | 128/165 |
| 3,762,405 | 10/1973 | De George | 128/88 |
| 3,831,467 | 8/1974 | Moore | 128/165 |
| 3,853,123 | 12/1974 | Moore | 128/165 |
| 3,856,008 | 12/1974 | Fowler et al. | 128/165 |
| 3,898,697 | 8/1975 | Whitehead | 128/88 |
| 3,955,565 | 5/1976 | Johnson | 128/89 R |
| 4,217,893 | 8/1980 | Payton | 128/165 |
| 4,387,709 | 6/1983 | Shen | 128/80 C |
| 4,465,064 | 8/1984 | Boone | 128/88 |
| 4,493,316 | 1/1985 | Reed et al. | 128/88 |
| 4,553,535 | 11/1985 | Finnieston et al. | 128/88 |
| 4,587,962 | 5/1986 | Greene et al. | 128/88 |
| 4,674,157 | 6/1987 | Litz | 128/80 C |
| 4,697,583 | 10/1987 | Mason et al. | 128/80 F |
| 4,716,892 | 1/1988 | Brunswick | 128/80 C |

Primary Examiner—Edgar S. Burr
Assistant Examiner—Huong Q. Pham
Attorney, Agent, or Firm—Kenyon & Kenyon

[57] ABSTRACT

A shell-like orthopedic brace is described which is divided into two halves and is prefabricated in various shapes and sizes. The measurement and applications of this device is used as required on any member of the patient's body. Two molded parts or shells are formed to the shape and size of the specific member or limb of the body where a brace is needed. The inside of each molded part or shell is fabricated to include cushionlike supports or suchioned areas of a soft material that are joined to the shell. These cushioned areas are placed between grooves in the shell. To provide air circulation, holes are positioned equally along the grooves and are opened through the shell.

Construction for the utmost safety, the left and right parts come together precisely. This construction makes the device very stable.

14 Claims, 1 Drawing Sheet

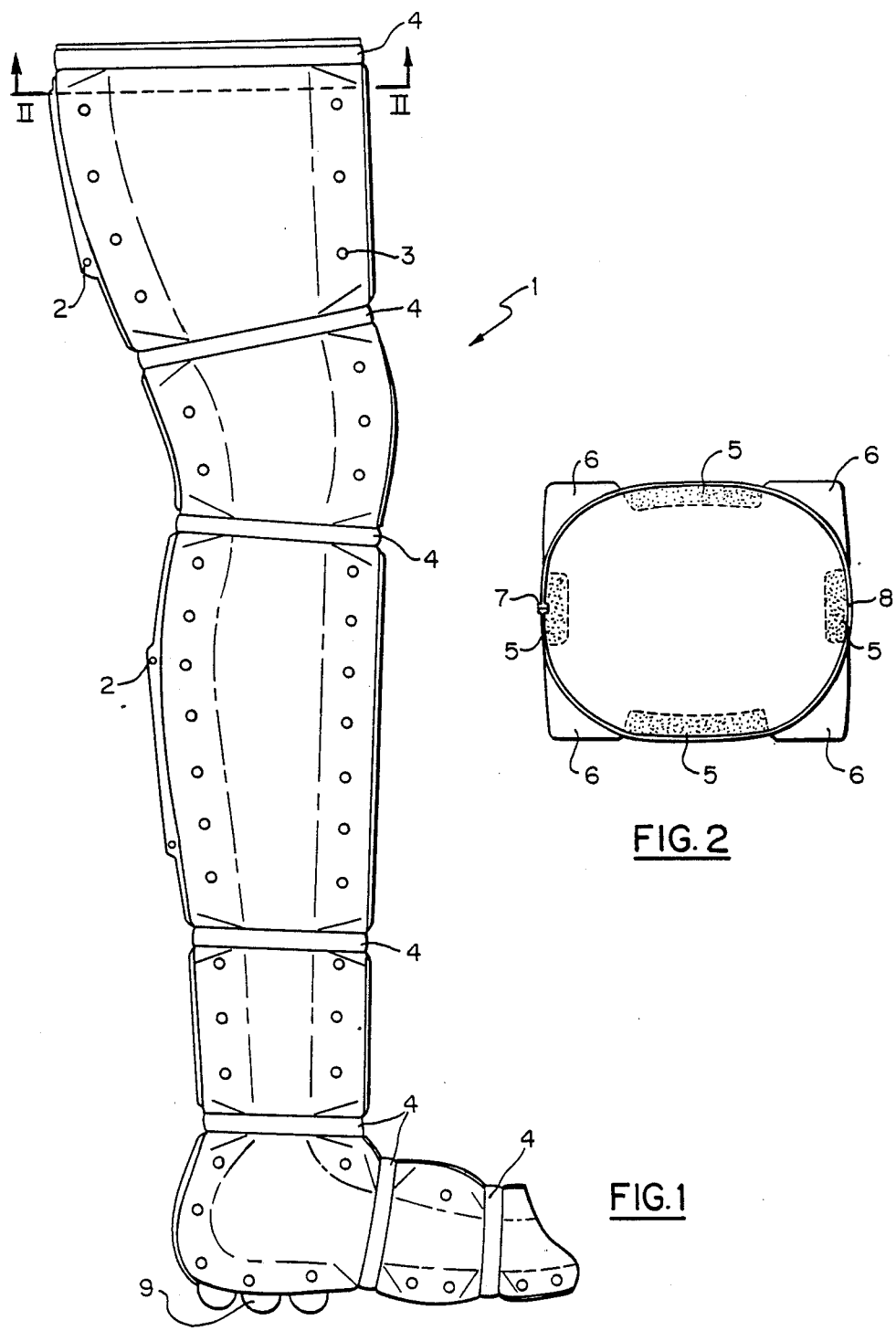

4,947,838

SHELL-LIKE ORTHOPEDIC BRACE

BACKGROUND OF THE INVENTION

1. Field of the Invention

This invention relates to a shell-like orthopedic brace which is produced in two halves more particularly to an orthopedic brace for curing the limbs of the human body and that of animals.

2. Disclosure Information Statement

In the past when a fracture occurred, to correct the situation the bone was set and a plaster cast was applied to allow the fractured area to fuse. In this manner, a technician working with the only medium available, namely plaster, first wrapped the broken limb in a bandage, then coated the site with plaster, and waited for the plaster to dry and cure.

Over a period of time, the formation of plaster casts has become the accepted way of curing fractures and an art practiced by many in the medical field, including orthpedic doctors, technicians, and nurses, and others on the orthopedic staff. While widely practical, it is well known that, when needed for long periods of time the plaster cast is inconvenient and cumbersome. Other disadvantages of the plaster cast are that plaster casts take a long time to prepare and must be applied by an orthopedic professional. When the cast is finished, the patient is carrying and supporting the weight of a closed heavy plaster cast. Other problems arise, such as personal hygiene, physical discomfort and psychological problems.

More specifically, with the plaster cast, it is difficult to nurse the fracture with medication or to observe the curing process. Further, it is difficult for the limb to breathe in a cast because there is no circulation or air. A patient with a plaster cast is also limited as to the extent of the personal hygiene he can manage as he must be careful not to get the cast wet. The difficulty with the psychological and the physical effects of the plaster cast is frequently related to the weight of the cast, the length of time the cast is used, and, the itching of the irritated areas.

Taking into consideration all of the above, one can see the advantages of the orthopedic brace fabricated in two shells the description of which follows.

SUMMARY OF THE INVENTION

The shell-like orthopedic brace of this invention is essentially constructed in two halves which combine of the following elements:

Two shells (halves) made to the form and measurement of the limb applied.

Inside each half (shell) are support cushions of a soft material attached to the shells and located between grooves.

Air holes are placed in anarray through the body of the two shells.

Constructed for safety the precision joints attach left and right half-shell forms to each other and thereby provide stability.

The orthopedic brace constructed in two sections is constructed so that one section is the mirror image of the other. The brace is preferably constructed of PVC, polyvinyl, polystyrene, or other reinforced plastic having the necessary physical properties.

The cushions, the grooves and the air holes are made in the configuration as shown, or variations thereof with an increase or decrease of holes and grooves as required by the application.

The cushioning (soft section) is fabricated from rubber, rubber foam, or plastic foam.

The oppositely corresponding portions of the border flange fit together reversibly in the two halves or sections. The holes are shown on the flange of the two shells.

The shells are optionally constructed with the bands or belts that are permanent which optionally may be used as the locking mechanism.

When compared to the conventional plaster cast, the orthopedic brace constructed in two halves, has more advantages like these:

Simple construction and low cost
Reduction in waiting time by 75%
Reduction in preparation time by 80%
Reduction in the number of steps administered
Ventilation to the injured limb through the air holes provided
Easier access to the injured limb for nursing, medical reasons, opening and closing
Re-usability of the orthopedic brace.
Reduces (1) precautions a patient must take with a cast. (2) Danger of misuse of plaster cast and (3) psychological problems connected therewith.

As stated hereinbefore the shell-like orthopedic brace has many advantages and can be readily applied in a variety of specific limbs. Other advantages of the orthopedic brace of this invention will become obvious from the reading of the detail description which follows, especially as the brace can be constructed in various forms and measurements and can be applied by relatively non-skilled workers to the limbs of the patient.

BRIEF DESCRIPTION OF THE FIGURES

The invention is more readily understood by viewing the figures that follow, in which similar parts are afforded the same reference designations in the various views.

FIG. 1 is a side view of the orthopedic brace.

FIG. 2 is a cross-sectional view of the orthopedic brace of FIG. 1, along section line II—II.

DESCRIPTION OF THE PREFERRED EMBODIMENT

Referring to FIGS. 1 and 2, an orthopedic brace for the human leg is shown, and referred to generally by the reference numeral 1. The orthopedic brace has an outer portion, inlcuding the border and flange. The orthopedic brace is structured to include two connected half shells or forms as shown. The orthopedic brace 1 is structured to include air holes 3. The two halves are connected by belts 4. The interior of the shells are constructed to include cushions of foam rubber 5. Channels or grooves 6 provide an airway along the length of the brace. Closure devices 7 and 8 indicate respectively the system for closing the orthopedic brace and attaching the "L" or "R" construction the one to the other. Semi-cylindrical heel supports 9 are shown attached to the heel portion of the leg brace for protecting the heel from shock and improving equilibrium.

In operation, when the brace is applied to the leg and is placed to the fracture correctly, the cushions 5 give the necessary precise pressure to the injured area. It has the ridged contact with the brace as with the skin. The function of the holes 3 and the grooves 6 is to assist in a continued flow of air into the brace and ultimately the injured area.

Although the best mode of the invention has been described herein in some detail, it has not been possible to include each and every variation. Those skilled in the art of constructing orthopedic braces will be able to make slight variations in the mechanical arrangement suggested hereby without departing from the spirit of the invention and still be within the scope of the claims appended hereto.

What is claimed:

1. A shell-like orthopedic brace for application to a specific limb of a patient, said orthopedic brace comprising in combination:

a first rigid half-shell form having front and rear edges, said first half-shell form being dimensioned to conform to the lateral side of said specific limb of the patient;

a second rigid half-shell form having front and rear edges, said second half-shell form being dimensioned to conform to the medial side of the specific limb of the patient for cooperative functional relationship with said first half-shell form, said second half-shell form being substantially a mirror-image of said first half-shell form and engageable therewith, said front edges of said first and second half-shell forms being engaged in abutting contact to each other at the front of the leg and said rear edges of said first and second half-shell forms being engaged in abutting contact to each other at the rear of the leg;

each said half-shell form comprising, in turn;
   one or more channel portions extending longitudinally along the shell form;
   air holes positioned along said channel portions in the shell and opening therethrough;
   support means of a soft material for attachment to each said half-shell form and for filling the interstice between said shell forms and said patient;
   each said support means secured by said channel portions of the half-shell forms; and
   means to maintain said two half-shell forms together in abutment around the specific limb of the patient, whereby, upon securing said orthopedic brace to said limb of the patient, the limb is securely supported by a lightweight, stable and well-ventilated brace.

2. The orthopedic brace as described in claim 1 wherein said means to maintain comprise belt means for securing said first half-shell form to said second half-shell form in an abutting manner the one with the other.

3. The orthopedic brace as described in claim 2 wherein said half-shell forms further comprise beltway means for accommodating said belt means, said beltway means being grooves extending about the perimeter of the brace.

4. The orthopedic brace as described in claim 1 wherein said first and second rigid half-shell forms are made of polyvinyl chloride.

5. The orthopedic brace as described in claim 1 wherein said first and second rigid half-shell forms are made of polystrene.

6. The orthopedic brace as described in claim 1 wherein said supports means are cushions that are held in place by said channel portions;

7. The orthopedic brace as described in claim 6 wherein said cushions are positionable at various locations along said channels as required by the specific limb of the patient.

8. The orthopedic brace as described in claim 7 wherein in addition to the preceeding the air holes in the channel portions are spaced at equal intervals therealong.

9. A shell-like orthopedic brace for application to a specific limb of a patient, said orthopedic brace comprising in combination:

a first rigid half-shell form having front and rear edges, said first half-shell form being dimensioned to conform to the lateral side of said specific limb of the patient;

a second rigid half-shell form having front and rear edges, said second half-shell form being dimensioned to conform to the medial side of the specific limb of the patient for cooperative functional relationship with said first half-shell form, said second half-shell form being substantially a mirror-image of said first half-shell form and engageable therewith, said front edges of said first and second half-shell forms being engaged in abutting contact to each other at the front of the leg and said rear edges of said first and second half-shell forms being engaged in abutting contact to each other at the rear of the leg;

each said half-shell form comprising, in turn;
   one or more channel portions extending longitudinally along the shell form;
   air holes positioned along said channel portions in the half-shell forms and opening therethrough;
   support means of a soft material for attachment to each said half-shell form and for filling the interstice between said shell forms and said patient; and,
   each said support means secured between said channel portions of the shell forms without impeding the flow of air to the limb; and
   means to maintain said two half-shell forms together in abutment around the specific limb of the patient, whereby, upon securing said orthopedic brace to said limb of the patient, the limb is securely supported by a lightweight, stable and well-ventilated brace.

10. The orthopedic brace as described in claim 9 wherein said means to maintain comprise belt means for securing said first half-shell form to said second half-shell form in an abutting manner the one with the other.

11. The orthopedic brace as described in claim 10 wherein said half-shell forms further comprise beltway means for accommodating said belt means, said beltway means being grooves extending about the perimeter of the brace.

12. The orthopedic brace as described in claim 9 wherein said supports means are cushions that are held in place by said channel portions.

13. The orthopedic brace as described in claim 12 wherein said cushions are positionable at various locations along said channels as required by the specific limb of the patient.

14. The orthopedic brace as described in claim 13 wherein in addition to the preceeding the air holes in the channel portions are spaced at equal intervals therealong.

* * * * *